Jan. 19, 1937. K. CARBAUGH Plant Pat. 222
ROSE
Filed July 1, 1936
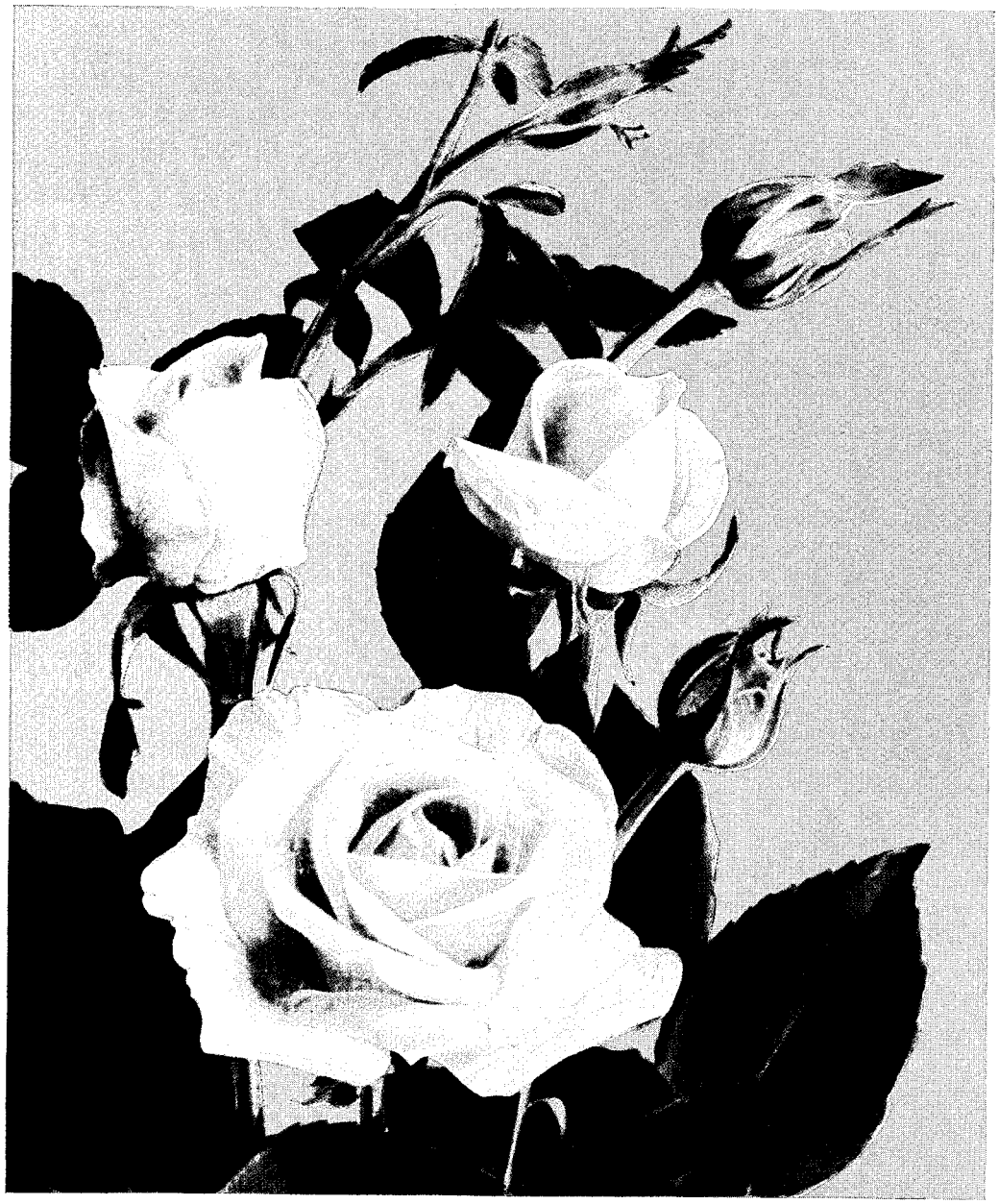
Inventor
Kellar Carbaugh
By Robert Robb
Attorneys Patented Jan. 19, 1937 Plant Pat. 222

UNITED STATES PATENT OFFICE

222

ROSE

Kellar Carbaugh, Lower Yoder Township, Cambria County, Pa., assignor to Johnstown Greenhouses, Inc., Johnstown, Pa.

Application July 1, 1936, Serial No. 88,461

1 Claim. (Cl. 47—61)

The present discovery relates to a new and distinct variety of rose plant—a sport of the well known "Rose Hill" variety.

The distinctive characteristics of this new rose may be best appreciated by a comparison of the same with those of its parent.

Insofar as the foliage of the plant is concerned, the leaves are much larger and darker green than Rose Hill, while the thorns are more curved and fewer in number to the stem.

The stem of this rose is characterized by its great length and thickness, enabling it to carry its bloom to better advantage. Without a pinch it will average 18" in length and with one pinch it will average 24".

As to the bud, that of the present variety is much larger, much more fragrant, and has an entirely different color than Rose Hill.

It is in the bloom, however, that the greater differences reside, among which may be noted: longer lasting bloom after cutting, in ordinary room temperature; many more petals, the number of Rose Hill being about 45 whereas the new rose has between 54 and 70; much larger size; and, unlike its parent bloom, does not lose its color under any weather conditions.

Another feature of importance in the new variety distinguishing it from its parent lies in the fact that it is a good producer in cloudy weather, bearing a very large percentage of blooms in the cold, short days of January and February.

The foregoing characteristics clearly indicate its distinctiveness and novelty, both with reference to its parent and similar prior known varieties.

Asexual reproduction has proven the characteristics to be fixed.

The following is a detail description of the new rose, wherein reference to color accords with the ordinary dictionary definition except where otherwise indicated:—

Parentage:

Sport of Rose Hill.

Classification:

Botanic and commercial—Hybrid tea.

*Flower*

Blooming habit:

Location where observations were made—Johnstown Greenhouses, Inc., Johnstown, Pennsylvania.

Date—During January.

Time of day—Afternoon, 2 p. m.

Blooms throughout the year and well in winter.

Bud:

*Size.*—Very large.

*Form.*—Long, pointed; unaffected by wet or hot weather.

*Color.*—(Ridgway's Color Standard). Bud color blends from a light "Scarlet Red" at tips through "Rose Doree" to "Lemon Chrome" at base.

*Sepals.*—Smooth edge; curl back.

*Calyx.*—Shape—pear. Size—large. Aspect—smooth.

*Peduncle.*—Aspect — smooth. Color — dark green. Strength—stiff.

*Opening.*—Bud opens well and is unaffected by adverse conditions.

Bloom:

*Size.*—Very large. Average size when fully expanded 3¼" to 4".

*Borne.*—Single.

*Stems.*—Long, strong.

*Form.*—When first open, high center. Permanence—outer petals curl back.

*Petalage.*—Very double (many petals and stamens hidden). Number of petals under normal conditions about sixty to seventy.

*Color.*—Flower is a beautiful "Deep Rose Pink" with a sheen to it,—"Rose Red", sometimes "Scarlet Red" in the depths, blending in the very bases of petals to "Lemon Chrome". (Ridgway's Standard.)

*Variegations.*—Veined.

*Discoloration.*—No discoloration, bloom carries through about ten days without losing color.

Petals:

*Texture.*—Fairly thick, unaffected by wet or hot weather.

*Appearance.*—Inside velvety. Outside satiny.

*Form.*—Slightly notched.

*Arrangement.*—Quite regular. Petaloids in center—few.

*Persistence.*—Hang on and dry.

*Fragrance.*—Strong. Nature—"Old rose perfume".

*Lasting quality.*—On the plant and as cut flowers very long.

Genital Organs:

*Stamens, anthers.*—Few, small.

*Stamens, filaments (threads).*—Medium. Color—gold yellow.

*Styles.*—Bunched.

Fruit:

*Sepals.*—Permanent, slightly pear shaped.

*Plant*

Form:

Bush.

Growth:

Very vigorous.

Foliage:

*Number of leaflets.*—5.

*Size.*—Very large.

*Quantity.*—Abundant.

*Color.*—New foliage—upper side—dark green with margins of "Mahogany Red" to "Garnet Brown" blending into the green. (Ridgway's Standard.) Under side—light green—does not fade. Old foliage—upper side—dark green. Under side—light green—does not fade.

*Shape.*—Oval pointed.

*Texture.*—Glossy, smooth. Under side—rough. Ribs and veins prominent

*Edge.*—Serrated (saw toothed).

*Serrations.*—Single, small.

*Rachis.*—Color green. Under side smooth.

Wood:

*New wood.*—Color—dark green. Bark—smooth.

*Old wood.*—Color—light green. Bark—fairly smooth.

Thorns (divided into thorns, prickles, and short needles):

*Thorns.*—Quantity—on main stalks—few. On laterals—few. Form—narrow, long, straight. Color when young—green and red. Position—irregular.

*Prickles.*—Quantity—on main stalks—few. On laterals—few. Color—green.

*Short needles.*—None.

I claim:—

The new and distinctive variety of rose plant, substantially as shown and described, characterized by the large size of its foliage, the size and length of its stem, the distinctive coloring of both bud and bloom, large size of bloom, its great fragrance, many petals, and lasting quality as a cut flower.

KELLAR CARBAUGH.